(12) United States Patent
Faulkner et al.

(10) Patent No.: US 6,692,426 B1
(45) Date of Patent: Feb. 17, 2004

(54) STERILE RADIOACTIVE SEEDS

(75) Inventors: Ian D. Faulkner, Amersham (GB); Thomas J. Rogers, Stoke Mandeville (GB)

(73) Assignee: Amersham PLC, Buckinghamshire (GB)

( * ) Notice: Subject to any disclaimer, the term of this patent is extended or adjusted under 35 U.S.C. 154(b) by 0 days.

(21) Appl. No.: 09/979,443

(22) PCT Filed: May 15, 2000

(86) PCT No.: PCT/EP00/04349
§ 371 (c)(1),
(2), (4) Date: Feb. 17, 2002

(87) PCT Pub. No.: WO00/74073
PCT Pub. Date: Dec. 7, 2000

(30) Foreign Application Priority Data

May 26, 1999 (EP) .............................. 99304067

(51) Int. Cl.$^7$ ........................... A61M 36/00; A61N 5/01
(52) U.S. Cl. ........................................... 600/8
(58) Field of Search ........................................ 600/1–8

(56) References Cited

U.S. PATENT DOCUMENTS

| | | | |
|---|---|---|---|
| 5,078,924 A | 1/1992 | Spinello | |
| 5,460,592 A | * 10/1995 | Langton et al. | 600/7 |
| 6,106,455 A | * 8/2000 | Kan | 600/7 |

FOREIGN PATENT DOCUMENTS

| | | |
|---|---|---|
| EP | 0 064 860 A | 11/1982 |
| EP | 0 386 936 A | 9/1990 |
| EP | 0 668 088 A | 8/1995 |
| JP | 11 113510 A | 4/1999 |

\* cited by examiner

*Primary Examiner*—Samuel G. Gilbert
(74) *Attorney, Agent, or Firm*—Li Cai

(57) ABSTRACT

Radioactive seeds, particularly 1–125 radioiodine seeds are sterilized by being subjected to dry heat at a temperature of at least 140° C., preferably 150–200° C. A container having loose sterile radioactive seeds therein is disclosed. The container is preferably of glass with a label and a removable heat-resistant silicone closure.

5 Claims, No Drawings

STERILE RADIOACTIVE SEEDS

The present invention relates to sterile radioactive seeds, and to a dry heat method for sterilising seeds. It is particularly concerned with sterile loose seeds which may be presented in a closed container, where the sterilisation method used is dry heat.

Radioactive seeds are radioactive permanent implants for the treatment (brachytherapy) of various clinical conditions, such as cancer, particularly prostate cancer, or restenosis. Such seeds comprise a radioisotope (typically $^{125}$I or $^{103}$Pd) sealed within a biocompatible container (typically titanium or stainless steel). Each patient dose is individually calculated depending on the size of the tumour, but is typically in the range 50–120 seeds per patient when treating prostate cancer. The seeds are implanted in a three-dimensional matrix according to calculated dosimetry. The seeds are sufficiently small to be loaded into implantation needles.

The radioactive-isotope of choice is $^{125}$I. This isotope has a half life of 60 days, short enough to permit implanted seeds to be left permanently in a patient's body without inflicting excessive long term damage. $^{125}$I emits low energy X-rays (30 KeV), which ensures that the volume of treated tissue is mainly confined to the locality of an implanted seed, i.e. the tumour.

In one currently available radioiodine seed, iodine-125 is adsorbed on to a silver rod and encapsulated in a welded titanium capsule. The silver rod acts as an X-ray marker. The seeds are cylindrical, 4.5 mm long and 0.8 mm diameter, designed to fit into a needle or catheter with an internal diameter of 1 mm. Such seeds are described in U.S. Pat. No. 4,323,055. These radioiodine seeds are commercially available. They are designed and manufactured to meet temperature test 5 of ISO 2919: 1999(E). This test involves holding the seeds at −40° C. for 20 minutes; at +600° C. for one hour; and subjecting the seeds to thermal shock from +600° C. to +20° C. It may be noted that these tests are designed simply to assess product safety performance when subjected to various stresses. Designs which do not release radioactivity pass the test. Hence such tests are not part of routine seed manufacture, but form part of the validation of a given seed design. Consequently, any deterioration in performance of the seed product as a result of the test, is not measured.

Brachytherapy seeds are commercially available in three forms:

a) loose, non-sterile, supplied in a screw cap vial;

b) sterile in a flexible suture;

c) sterile in a stiffened suture.

The last product (sold under the RapidStrand trademark) comprises an initially flexible elongated bio-absorbable material having seeds incorporated therein at regular intervals. The strand is subsequently heated which makes it less flexible, to aid the process of implanting in or around a tumour. As noted in U.S. Pat. No. 5,460,692, this RapidStrand product is marketed in a sterile state by virtue of having been treated with a chemical sterilising agent. However, chemical sterilisation is problematic as discussed below and is not suitable for loose seeds.

It may be noted that, despite being radioactive, the radioiodine seeds are not self-sterilising. This is because the radiation dose at the surface of the seed is insufficient to cause the required degree of killing of micro-organisms. Customers who buy non-sterile loose radioiodine seeds need to sterilise them before use. An instruction leaflet accompanying the seeds teaches the use of steam sterilisation and specifically advises against the use of dry heat or chemicals to sterilise the seeds. However any unnecessary manipulation of radioactive seeds by a customer is inherently undesirable. Since the seeds contain a volatile radioiodine isotope, any handling operation that involves heating is particularly undesirable. Moreover regulations in Europe do not permit the sale of radioactive seeds in a non-sterile form if they are to be permanently implanted in the human body. There is thus a need for a supply of loose sterile radioactive seeds. This invention addresses that need.

In one aspect the invention provides a method of sterilising one or more radioactive seeds. The method comprises subjecting the radioactive seeds to dry heat for a time sufficient to effect sterilisation; and subsequently cooling the radioactive seeds. The temperature of the dry heat sterilisation process should be at least 140° C., preferably 150–200° C., most preferably 160–165° C. The term 'dry heat' is used in the field of sterilisation, and denotes that the heating is achieved without contacting the seeds with either boiling water or steam, ie. in contrast to moist heat. The term 'cooling' encompasses both a passive process (eg. removing or switching off the source of heat) so that the seeds cool slowly to ambient temperature, and a more active process (eg. moving the seeds to a cooler area, or application of a cooling means such as a fan), so that the seeds cool more quickly.

In another aspect the invention provides a product prepared by the above dry heat sterilisation process. The product comprises one or more radioactive seeds in a sterile condition, preferably in a closed container, wherein the seed(s) have been sterilized by dry heat.

In another aspect, the invention provides a product comprising a closed container containing one or more radioactive seeds in a sterile condition, wherein the radioactive seeds are free of moisture and of chemical residues characteristic of chemical sterilisation, and wherein the product is free of degradation characteristic of sterilisation by gamma irradiation.

The dry heat process of the present invention may be carried out by use of a variety of heating means capable of achieving the required substantial absence of moisture and temperature control for the required time, such as ovens (heated by conventional means such as electricity, gas or solid fuel); radiant heat (eg. from hot wire filaments); immersion in a bath of heated high-boiling organic solvent (eg. an oil such as silicone); flames; or infra-red radiation. Heating techniques which require an additional step, such as the removal of residual high-boiling solvent or surface combustion deposits are less preferred. It is preferred to use ovens, which may be electrically or gas heated, and deliver heat via hot air, and which have a temperature-controlled environment. Microwave ovens not suitable, since such heating is not safe for metallic objects such as seeds, potentially risking rupture of the seed. Also, microwave heating would deliver heat to the inside of the seed, whereas the present invention requires that the outer surface of the seed is heated to sterilise that part of the seed which would be in contact with the human body. Ovens suitable for use in the present invention are commercially available in a variety of forms and sizes, and are preferably heated electrically and designed for laboratory use.

The dry heating of the present invention should preferably be carried out in an atmosphere which contains oxygen, and is preferably and conveniently carried out in air. The presence of oxidation facilitates the destruction of micro-organisms by an oxidative process. When the heating means is an oven, hot air is used to transfer the heat to the seeds to be sterilized. Hence, when the seeds are sterilized in a closed container, the headspace gas above the seeds in the container should contain oxygen, and is preferably and conveniently air at atmospheric pressure.

Whichever heating means is used, it is necessary to have adequate temperature control around the zone in which the seeds are to be heated. This temperature control may be achieved either manually, eg. by adjustment of the heat in response to temperature readings, or is preferably achieved automatically via a thermostatically controlled heating means, preferably as part of a temperature-controlled oven. The temperature at specific locations within the heating means used (eg. different areas or shelves within an oven), should be validated prior to use to show that the temperature delivered at the heating zone around the location(s) of the seeds is that required by the present invention. Once the coolest part of the heating zone used has been established, the temperature probe used during the dry heat sterilisation should always be located at that position, to ensure that the required minimum temperature is always achieved. The effectiveness of the sterilisation cycle at all parts of the heating-zone should be validated by demonstrating that authentic samples of micro-organisms at the various locations are killed, eg. by showing that, when cultured following the dry heat cycle, there is no growth. The temperature readout may preferably be recorded (eg. as a graphical printout or electronic record) during the dry heat sterilisation process. This record can usefully be included as part of the batch records as evidence of sterilisation of the seeds.

The duration of the dry heating is dependant on the temperature adopted. The British and European Pharmacopoeias recommend a minimum holding time of 120 minutes at a temperature of at least 160° C. for dry heat sterilisation. Shorter minimum holding times may conceivably be used at higher temperatures, eg. approximately 60 minutes at 170° C., and 30 minutes at 180° C., but it is preferred to adopt the Pharmacopoeia protocols. The timing of the dry heating can be carried out manually, or is preferably carried out automatically using a suitable oven having temperature programming controls, eg. microprocessor-controlled.

Preferably, the seeds are loose. Preferably the seeds are provided in a closed container, of glass or a plastic material capable,of withstanding the sterilisation temperature. While a sealed glass ampoule can be used, the container is preferably a glass vial having a removable closure e.g. made of silicone or other material capable of withstanding the sterilisation temperatures involved. The closure must be gas tight and is normally anchored in position with an overseal, which is typically crimped on and metallic in nature. Such an arrangement ensures that the environment around the sterile seeds within the container is maintained. For ease of handling by a customer, loose seeds present within a container are preferably in a drystate.

The radioactive seeds of the present invention may also have been modified so that they are echogenic, ie. they reflect ultrasound of clinical frequency (ca. 7.5 MHz) over a wider range of angles to the ultrasound transducer than conventional seeds. Such echogenic seeds may have at least a portion of their outer surface roughened, as described in commonly assigned application PCT/GB99/03668. The roughening may take the form of grooves, depressions, scratches or the like on the surface of the seed container. The grooves may be arranged randomly on the surface or in more regular patterns eg. in geometric shapes and patterns such as squares and circles, or as lines running substantially parallel or perpendicular to an axis of the seed or in a helical arrangement. Preferably, the grooves etc. are not arranged in a highly repeating pattern with more than one repeat per quarter wavelength as such patterns may act as optical gratings and lead to a loss of omnidirectionality in the echo return. Preferably, the irregularities or discontinuities are in the form of a helical groove (eg. with a sinusoidal profile) on the surface of the container. The pitch of the helix may be chosen to give first order maxima in the intensity of the reflected ultrasound at certain specific angles with respect to the orthogonal orientation. For example, for a conventional radioactive seed 4.5 mm long and 0.8 mm in diameter, a pitch of about 0.6 mm will give a maximum at 10° from orthogonal with 7.5 MHz ultrasound, whilst a pitch of about 0.3 mm will give a maximum at 20° from orthogonal. For such a seed the depth of the groove from peak to bottom should be approximately 40 to 60 $\mu$m. The spacing of repetitive grooves along a source's axis should not be too close, otherwise a minimum of ultrasound scattering may occur at angles close to 90° (i.e. orthogonal). The roughening may be produced by a variety of different methods. Thus, the outer surface of the seed container may be roughened or shaped by forcing the source through a ridged or serrated dye or a threading device to impart grooves on the surface. A similar effect may be produced by milling. The surface may also be roughened as a result of mechanical friction, for example by use of a wire brush or a file, or a suitable grade of sandpaper, e.g. a coarse grade. The outer surface may also be etched, for example using a laser or water-jet cutter, or by electrolytic etching. Blasting, for example sand blasting, may also be used. Blasting may be done dry or wet as in water-jet blasting.

Batches of radioactive seeds, comprising different numbers of radioactive seeds in the range 1–200, e.g. 1–100, preferably 1–50 radioactive seeds, may be sterilized using the method of the present invention. Preferably these batches are provided in closed containers each of which carries during sterilisation a label or marker indicating the contents of the closed container.

The choice of dry heat for sterilising radioactive seeds was not an obvious or a natural one. To illustrate this, there follows a discussion of the various sterilisation methods available. The principal choices are:

(i) aseptic handling,
(ii) steam sterilisation,
(iii) steam (porous load),
(iv) chemical (e.g. ethylene oxide),
(v) gamma irradiation,
(vi) dry heat.

(i) Aseptic Handling

This is one approach for producing sterile seeds. In effect this means that the whole seed manufacture process is carried out under aseptic conditions (clean rooms, air filtration etc). This is not an attractive prospect since it makes manufacture difficult, labour-intensive and expensive especially when radioactive safety and handling precautions are also necessary. Hence so-called 'terminal sterilisation' (i.e. sterilisation only after all the components have been assembled in a non-sterile environment) is much preferred. (ii)–(vi) are the principal options for terminal sterilisation.

(ii) Steam Sterilisation (Moist Heat).

This is typically carried out using an autoclave. This process involves the use of moist heat, usually as saturated steam at temperatures above 100° C. This achieves the destruction of micro-organisms by the irreversible denaturation of enzymes and structural proteins of the microorganism. When a sealed container of loose seeds is to be sterilized, the implication is that there must be water within the closed container. This is to ensure good heat transfer, ie. steam must condense on the surfaces. The phase change is responsible for the dispersion of energy, ie. the condensation of the steam releases heat which is imparted to the surface. This means that, although sterile, the product to be shipped to the customer would be wet within the container/vial. For a vial in which loose seeds are currently sold, it is estimated that ca. 0.5 cm$^3$ of water would be required in a vial of 10 cm$^3$ volume. This in itself makes for an unattractive product, and poses handling problems for the clinician, who must dry the seeds before use etc.

An unforeseen problem with this is that in transit (e.g. when being shipped in cold climates or in aircraft holds), the water may freeze causing great pressures which may be sufficient to risk rupturing the welds of the seeds. Thus, although steam sterilisation is a standard technique, it has significant disadvantages when applied to the commercial supply of sterile loose seeds (which need to be shipped within a container, containment or packaging to maintain the sterile integrity in transit).

If steam sterilisation is used in conjunction with an open vial of seeds, then additional steps become necessary—first to dry the inside of the vial, and then to stopper the vial under aseptic conditions. Hence this then becomes no longer the preferred 'terminal sterilisation' step, but requires further sterile handling procedures.

(iii) Steam Sterilisation (Dorous Load).

Steam sterilisation may conceivably be used with suitably porous closures/stoppers to permit ingress and egress of the steam, but this poses significant technical problems in ensuring complete removal of residual water and additional shielding or secondary containment required in case there is a leak of radioactivity from any of the seeds.

(iv) Chemical. e.g. Ethylene Oxide (EtO).

Ethylene oxide gas (EtO) is used to sterilise some seed products, eg. Nycomed Amersham's RapidStrand. Use of this material has several serious problems. First it is highly toxic, hence thorough degassing to ensure that removal of EtO is complete is essential. It is also inflammable,—a significant risk when being used in conjunction with radioactive plant. As a consequence of the need for thorough degassing, sterilisation using EtO is slow. As with (iii) above, porous packaging materials Would be required to use EtO for terminal sterilisation. EtO is also known to leave trace organic residues (ethylene oxide itself, ethylene chlorohydrin, ethylene glycol and ethylene oxide condensation polymers) on the surface of the materials sterilized.

Manifestly, chemical sterilisation of a closed container is not effective to sterilise the contents of the container. If radioactive seeds are subjected to chemical sterilisation, they must be introduced into closed containers subsequently and this adds complications to the process.

Other chemical alternatives to EtO exist, but direct use of liquid chemicals on the seeds runs the risk of damage to the seed capsule; especially to the weld with attendant risk of radioactive leakage etc. As with EtO, there is also the issue of both achieving and demonstrating complete removal of the chemical used since the seeds are destined to be implanted in the human body.

There is also the possibility that some chemical treatments, can render the outer surface of the seeds 'sticky', which would make subsequent loading into needles and implantation by the user more difficult.

(v) Gamma Irradiation.

Irradiation with a high energy gamma emitter (e.g. $^{60}$Co) is a standard technique used for the terminal sterilisation of medical materials. A problem with this approach is that significant plant is required, with heavy shielding of the gamma-emitting radioisotope. It is also the case that conventional gamma irradiation plant is not configured to deal with products which are themselves radioactive. Hence there are problems of suitable containment and shielding etc, for a significant volume of gamma irradiation plant and equipment. It may be also that some parts of the seed packaging may be damaged by the high energy gamma rays. Thus if glass materials are used (e.g. a vial), the glass would be browned in colour by the irradiation. Any labels on the materials would probably also be discoloured.

(vi) Dry Heat

This method involves heating a product at a temperature of at least 140° C., preferably 150–200° C., preferably at least 160° C. Sterilisation in this case is believed to occur via oxidation of the microorganism cell constituents. Sterilisation using dry heat is known to require higher temperatures and longer exposure times than moist heat. The product is held at the temperature for a time sufficient to effect sterilisation, typically for a minimum of 2 hours, and is then cooled or allowed to cool.

The dry heat seed sterilisation process of the present invention has the advantage that it is quick, uses equipment typically found in a production laboratory, is relatively easy to validate and control, and gives a very high sterility assurance level. The sealed seed container does not need to be open during the process, hence it is a genuine terminal sterilisation. There is no need for specific assays or checks to ensure removal of toxic chemicals, and the product is in a form which is convenient to use for the customer.

As discussed, this approach to seed sterilisation is not one which would be immediately apparent. Strong heating of a sealed capsule containing a volatile radionuclide does imply an attendant risk of internal pressure developing. Clearly any rupture of the capsule or weld would cause a serious escape of radioactivity. The greater the number of seeds heated in this way, the greater would be the perceived risk of problems arising. It is also the case that, depending on how it is done, seeds which are very small (cylinders ca. 4.5 mm long×0.8 mm diameter), radioactive and hot (temperature) present significant handling problems.

As previously noted, currently available radioactive seeds can withstand heating to 600° C. for one hour plus thermal shock from 600° C. to +20° C. without loss of radioactive integrity. However, it would be anticipated that such heating might change the chemical nature of the radioisotope within the seed (eg. via oxidation), or redistribute the radioisotope within the seed, leading to a change in the radiation dosimetry contours ("isodose curves") around the seed. Although dose distribution around each individual seed is not perfectly isotropic, substantially uniform dosimetry is important for the desired medical treatment, hence any such change would compromise the efficiency of the product. In tests to validate the present invention, it has been determined that dry heat sterilisation for 2 hours at 160° C. does not compromise the substantially isotropic dose distribution around each individual radioiodine seed, and the same would be expected to be true for $^{103}$Pd seeds.

Preferred closed containers according to this invention are glass vials with septum seals or other rubber or plastic closures. A problem with such rubber or plastic closures in general is that strong heating can promote leaching of unwanted organic impurities from the closure, potentially contaminating the seeds. Clearly this would be very unsatisfactory for a medical product. Also the closure not deform on heating, i.e. the seal must be maintained. Many standard vial closures simply would not withstand the temperatures necessary for dry heat sterilisation. One silicone closure has been identified which has the necessary properties. That is a silicone stopper 1185 marketed by The West Company Danmark AS, and reported to be made from a liquid silicone rubber Silastic® 9280/40E.

In normal pharmaceutical manufacture, batches typically comprise multiple units of the same material. For the present product, the situation is different. This is because the physician orders a variable number and/or activity of seeds depending upon his/her calculation of the dosimetry required for the individual patient therapy. Consequently, each closed container to be dry heat sterilized may contain either a variable number of seeds (e.g. from 1 to 50), or the same number of seeds but of a different activity level, i.e. each container is different. Preferably a plurality of containers of radioactive seeds, comprising the same or different numbers or activities of radioactive seeds, are sterilized together. This can conveniently be achieved by eg. loading the containers into a tray which can then be loaded into the oven or other means used to supply the dry heat.

The variable number and/or activity of seeds means that the labelling of radioactive content, dose at extremities of the packaging etc. could be very different. As a result, it is convenient to have traceability of an individual vial right through the process. Thus it is preferred that the seed container is labelled or otherwise marked to show the number of seeds contained, radioisotope activity content etc in such a way that the mark or label remains in place during the dry heat sterilisation step. As might be expected, many paper-based labels do not withstand the oven temperatures used and darken in colour, going brown. This is obviously undesirable for the product presentation. Similarly, whatever printing method is used for the labels must also be able to withstand the conditions without loss of information. The solution to this problem is the use of particular plastic labels, having printing thereon that can withstand the heat. Thermal transfer ribbons based on coated white polyester film and marketed by Armor under the Trademark AXR7, have been found suitable for use in the present invention.

The invention is illustrated by the following non-limiting Examples:

Example 1 describes a preferred method of carrying out the dry heat sterilisation process of the present invention.

EXAMPLE 1

1 to 50 $^{125}$I seeds were transferred to an open P6 glass vial. The vial was sealed in air at atmospheric pressure with a silicone closure, and an overseal crimped on using a pneumatic crimper. The vial was transferred to a laboratory oven (LTE Scientific, Swallow model) at ambient temperature, and the oven door closed. The oven temperature was monitored using a temperature probe located in the coolest part of the oven. A temperature programme was then initiated whereby the oven temperature was raised to 165° C., maintained at that temperature for 135 minutes, and then the heat was switched off and the oven allowed to cool slowly back to ambient.

What is claimed is:

1. A method of sterilising one or more radioactive seeds, which method comprises subjecting the radioactive seeds to dry heat at a temperature of at least 140° C. for a time sufficient to effect sterilisation, and subsequently cooling the radioactive seeds, wherein the radioactive seeds are in a closed container, which is a vessel having a removable gas impermeable closure.

2. A method of sterilising one or more radioactive seeds, which method comprises subjecting the radioactive seeds to dry heat at a temperature of at least 140° C. for a time sufficient to effect sterilisation, and subsequently cooling the radioactive seeds, where the seeds are echogenic.

3. A product comprising one or more sterilized radioactive seeds wherein the seeds are sterilized by dry heat sterilization process which comprises subjecting the radioactive seeds to dry heat at a temperature of at least 140° C. for a time sufficient to effect sterilisation, and subsequently cooling the radioactive seeds, wherein the radioactive seeds are in a closed container, wherein the closed container is a vessel having a removable gas-impermeable closure.

4. The product of claim 3 wherein the vessel is of glass and the removable gas-impermeable closure comprises silicone.

5. A product comprising one or more sterilized radioactive seeds wherein the seeds are sterilized by dry heat sterilization process which comprises subjecting the radioactive seeds to dry heat at a temperature of at least 140° C. for a time sufficient to effect sterilisation, and subsequently cooling the radioactive seeds, wherein the seeds are echogenic.

* * * * *

UNITED STATES PATENT AND TRADEMARK OFFICE
CERTIFICATE OF CORRECTION

PATENT NO. : 6,692,426 B1 Page 1 of 1
DATED : February 17, 2004
INVENTOR(S) : Ian D. Faulkner and Thomas J. Rogers It is certified that error appears in the above-identified patent and that said Letters Patent is hereby corrected as shown below:

Title page,
Item [57], ABSTRACT,
"1-125" should read -- I-125 --

Signed and Sealed this

Third Day of August, 2004

JON W. DUDAS
*Acting Director of the United States Patent and Trademark Office*